(12) United States Patent
Cholet

(10) Patent No.: US 7,174,770 B2
(45) Date of Patent: Feb. 13, 2007

(54) METHOD AND DEVICE FOR AUTOMATIC DETERMINATION OF THE PERMEABILITY OF A POROUS MATERIAL HAVING ALTERNATING LEVELS OF POROSITY

(75) Inventor: Georges Cholet, Ormes (FR)

(73) Assignee: Societe Nationale d'Exploitation Industrielle des Tabacs et Allumettes (FR)

( * ) Notice: Subject to any disclaimer, the term of this patent is extended or adjusted under 35 U.S.C. 154(b) by 351 days.

(21) Appl. No.: 10/488,234

(22) PCT Filed: Aug. 8, 2002

(86) PCT No.: PCT/FR02/02828

§ 371 (c)(1),
(2), (4) Date: Feb. 26, 2004

(87) PCT Pub. No.: WO03/019132

PCT Pub. Date: Mar. 6, 2003

(65) Prior Publication Data

US 2004/0187560 A1 Sep. 30, 2004

(30) Foreign Application Priority Data

Aug. 28, 2001 (FR) .................................. 01 11288

(51) Int. Cl.
*G01N 15/08* (2006.01)
(52) U.S. Cl. ........................................... 73/38; 73/159
(58) Field of Classification Search .................... 73/37, 73/38, 159; 131/365; 229/87.12, 87.13, 229/87.14
See application file for complete search history.

(56) References Cited

U.S. PATENT DOCUMENTS

| | | | | |
|---|---|---|---|---|
| 3,709,028 A | * | 1/1973 | Doerman | 73/38 |
| 4,246,775 A | * | 1/1981 | Stultz | 73/38 |
| 4,651,557 A | * | 3/1987 | Cholet | 73/38 |
| 5,474,095 A | * | 12/1995 | Allen et al. | 131/365 |
| 5,878,753 A | * | 3/1999 | Peterson et al. | 131/365 |
| 5,878,754 A | * | 3/1999 | Peterson et al. | 131/365 |
| 5,893,372 A | * | 4/1999 | Hampl, Jr. | 131/365 |
| 5,921,249 A | * | 7/1999 | Hampl, Jr. | 131/365 |
| 6,212,941 B1 | * | 4/2001 | Cholet | 73/38 |
| 6,568,403 B2 | * | 5/2003 | Hampl et al. | 131/365 |

FOREIGN PATENT DOCUMENTS

| | | | | |
|---|---|---|---|---|
| EP | 486213 A1 | * | 5/1992 | |
| GB | 2100572 A | * | 1/1983 | |

* cited by examiner

*Primary Examiner*—Hezron Williams
*Assistant Examiner*—David A. Rogers
(74) *Attorney, Agent, or Firm*—William A. Drucker

(57) ABSTRACT

A method and device for using a permeameter comprising a measuring head (2) opposite which the sheet or strip (1) is displaced step by step. The method and device can comprise a registration including the determination of the permeability profile of the strip (1) over a period T including two different successive permeability ranges, determination of a sinusoid from said profile, the of two extremes of said sinusoid, centering the measuring head (2) on the second extreme, and moving the strip step by step by T/2 and, at each step, performing a permeability measurement.

7 Claims, 2 Drawing Sheets

METHOD AND DEVICE FOR AUTOMATIC DETERMINATION OF THE PERMEABILITY OF A POROUS MATERIAL HAVING ALTERNATING LEVELS OF POROSITY

BACKGROUND OF THE INVENTION

This present invention concerns a method and a device for automatic determination of the permeability of an object of porous material, where this object can come in the form of a sheet or a strip of porous material consisting of successive segments which alternately present different levels of permeability according to a pre-established periodicity.

It applies particularly, though not exclusively, to monitoring and measurement of the permeability of the segments of a paper strip of the type such as described in patent EP 0486213 A1 with cellulose type fiber weave, which consists of a succession of transverse segments of different densities and therefore of different permeability. This paper strip can be used, for example, for the production of self-extinguishing cigarettes.

In general, it is known that the permeability of a sheet of porous material can be ascertained by means of a permeability meter consisting of a measuring head with two tubular parts that move in relation to each other, in such a way as to butt up against each other in order to grasp the sheet, thereby respectively delimiting two coaxial chambers on two distinct faces of the material. One of these chambers is connected to a measurement circuit consisting of a flowmeter, pumping resources capable of creating a pressure or a vacuum in the measurement circuit, and regulation resources capable of maintaining a determined pressure in the measurement circuit.

The manufacturers of strips of porous material of the aforementioned type, and also the users of such strips, wish to be able to monitor the permeability of the porous segments of the strip by means of a measurement at the center of each strip, regardless of whether this is a segment of low permeability or a segment of high permeability.

In order to achieve such results, the following two conditions must be satisfied:

the use of a measuring head whose chambers are of smaller dimensions than those of the segments, so that when the two chambers are centered on a segment, the measurement will be effected only at a central zone of this segment, and implementation of the method and device which allow the measuring head to be centered on each of the segments whose permeability is to be measured.

The first of these conditions is easily satisfied if the dimensions of the segments are known. In practice, these will be supplied by the paper manufacturers.

However, the second condition gives rise to a significant problem because of the fact that the porous segments of the strips are not visible, and so it is not possible to initialize the position of the strip by a visual reference.

OBJECT OF THE INVENTION

The particular subject of the invention is therefore a method for the determination of permeability, which solves this problem effectively, and which does this in a fully automatic manner.

To this end, it begins with the observation that it is possible to make the permeability profile of the strip coincide with a sinusoidal (obtained by a sinusoidal regression from this profile) whose ends determine the position of the centers of the segments concerned.

SUMMARY OF THE INVENTION

As a consequence, the method according to the invention consists of the following.

Firstly, a preliminary stage is performed which comprises determination of the permeability profile of the strip over a length of material of period T covering two successive segments, the determination of a sinusoid by sinusoid regression from the profile obtained, determination of the position of both ends of this sinusoid, and centering of the measuring head on these two ends;

Next, a measuring stage consisting of advancing the paper strip in steps of T/2, with a permeability measurement at each step.

Determination of the permeability profile, effected in the preliminary stage can be accomplished by performing two successive permeability measurements in a period which is much shorter than the period T, e.g., millimeter-by-millimeter.

The sinusoidal regression done in this phase can be achieved by employing the method of least squares using values obtained when determining the permeability profile.

The invention, of course, also provides a device for the implementation of this method.

BRIEF DESCRIPTION OF THE DRAWINGS

One method of execution of the invention will be described below, as a non-exhaustive example, with reference to the appended drawings, in which.

DESCRIPTION OF THE PREFERRED EMBODIMENTS

Figure 1:
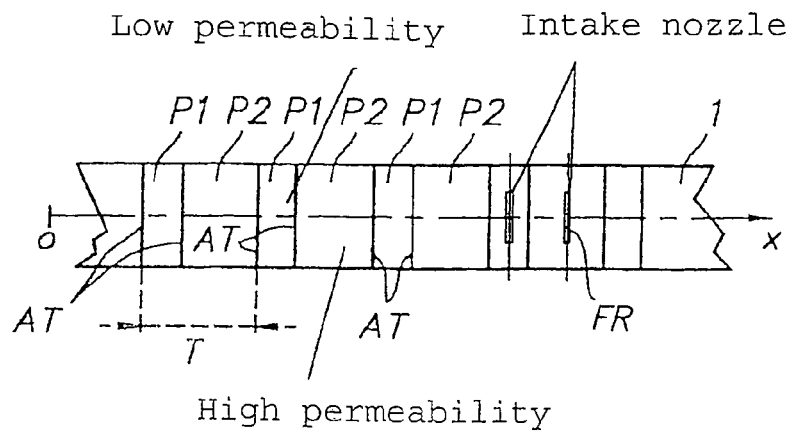
FIG. 1 is a top view of a paper strip, showing the successive segments of low and high permeability.

In the example represented in FIG. 1, the paper strip 1 is a cigarette paper with two series of alternating segments, $P_1$ and $P_2$, with two different permeabilities, so as to achieve self-extinction of abandoned cigarettes.

Segments $P_1$ and $P_2$ extend perpendicularly along axis OX of strip 1. The low permeability segment $P_1$ has a width which is less than that of the high permeability segment P2. This strip can be made according to the production method described in the aforementioned patent EP 0486213 A1.

Figure 2:
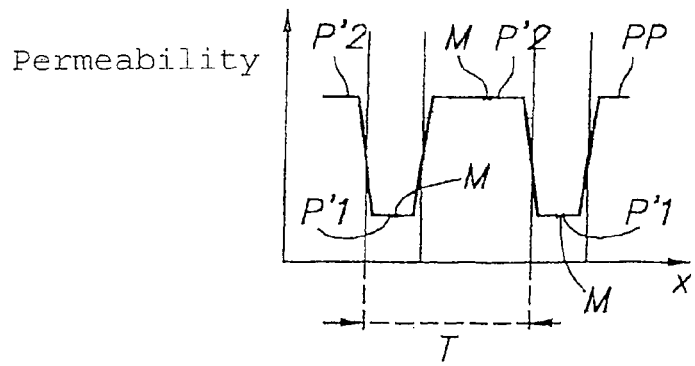
FIG. 2 is a diagram showing the permeability profile of the strip over the period of T.

As mentioned previously, the successive segments $P_1$ and $P_2$ of the strip cannot be distinguished visually (the separation lines shown in FIG. 1 do not exist physically). As a consequence, the only option for positioning of the strips is to measure, point by point, e.g., millimeter-by-millimeter, the permeability of the strip along the longitudinal axis OX, so as to obtain a permeability profile PP such as that indicated in FIG. 2. This profile is of crenellated form, i.e., it consists of low levels $P'_1$ corresponding to segments of low permeability $P_1$, and high levels $P'_2$ corresponding to segments of high permeability $P_2$. These levels $P'_1$ and $P'_2$ are connected together by ramps corresponding to the transition zones between the successive segments $P_1$ and $P_2$.

It is clear that determination of the centers M of the levels $P'_1$ and $P'_2$ of the profile obtained enables the position of the transverse median axes AT of segments $P_1$ and $P_2$ to be obtained.

Figure 3:
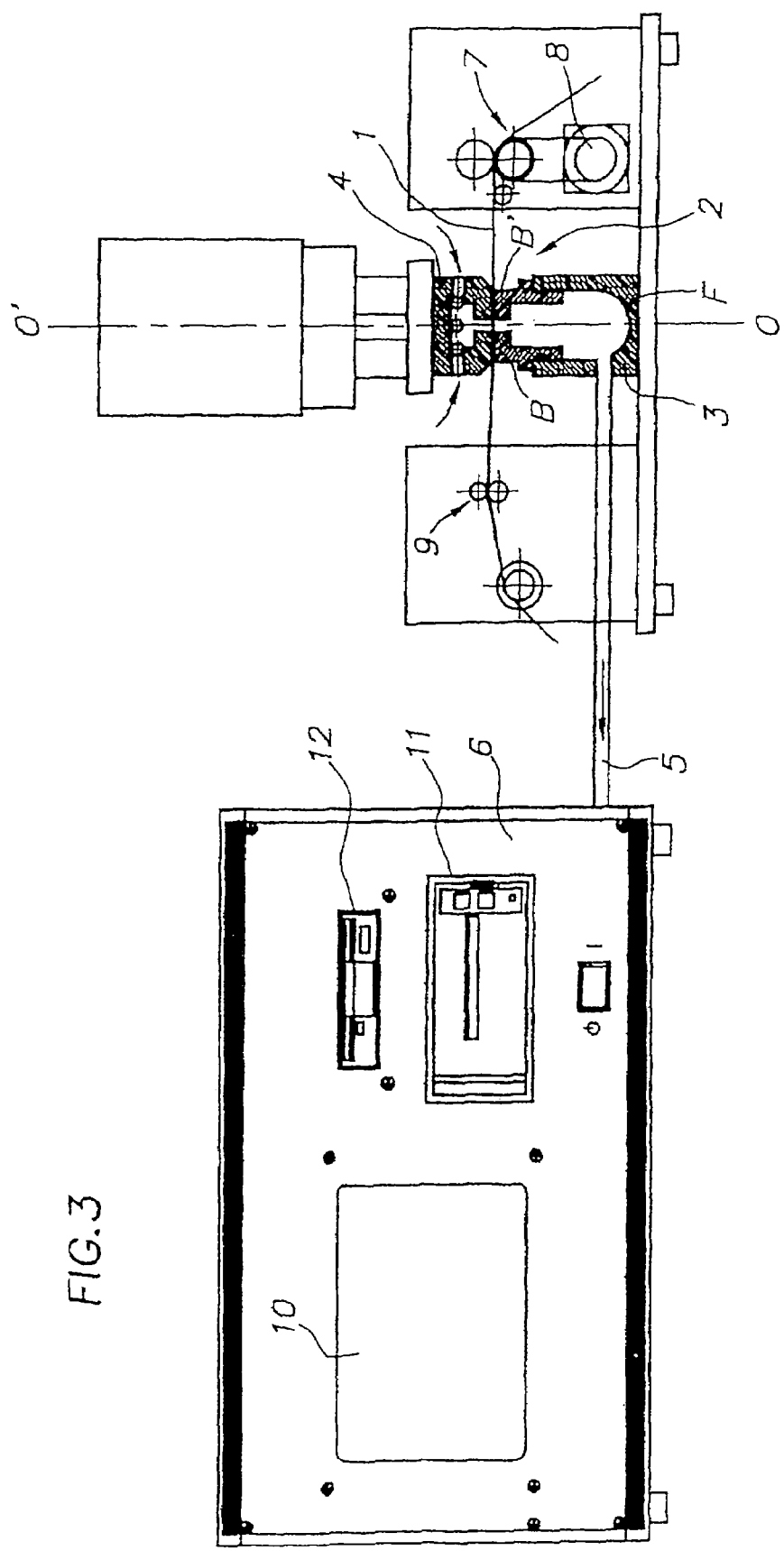
FIG. 3 is a schematic section view of a device for automatic determination of the permeability of a paper strip of the type represented in FIG. 1.

As shown in FIG. 3, the device for automatic determination of the permeability of the paper strip 1 comprises a measuring head 2 which has two tubular parts 3 and 4 with virtually the same dimensions, between the strip 1 passes. These two tubular parts 3 and 4 move in relation to each other, and can be placed coaxially opposite to each other so that they can butt together, thereby grasping the strip 1 between their edges B and B'. Advantageously, these edges B and B' can be equipped with a covering which is used to guarantee a good seal between the two parts 3 and 4 of the paper strip 1.

Tubular part 4 is open at its two ends, while tubular part 3 has a bottom 3 located at the end opposite to edge B', so as to constitute an intake chamber closed off by the strip 1.

This chamber is connected to the intake tube 5 of a conventional permeability meter 6 of the type, for example, described in patent FR 2 773 882 submitted in the name of the present applicant.

As shown in FIG. 1, in this example, the edges B and B' of the two parts of the head delimit the shape of a rectangular slot FR, whose width is very much less than the width of a segment $P_1$ or $P_2$, while the length remains less than the width of the strip 1.

The strip 1, usually fed in via a roller, is guided at each side of the measuring head 2 by two roller systems, namely a system of driving rollers 7 driven by a stepping motor 8, and a system of guide rollers 9 used for guidance and tensioning of the portion of the strip 1 passing between the two parts 3 and 4 of the measuring head 2.

The stepping motor 8 is designed so that it can function in two different modes, namely:

a first mode in which each step caused an advance of the strip 1 by one millimeter, a second mode in which each step causes an advance of the strip 1 equal to half the sum of the width of a high permeability segment $P_2$ and the width of a low permeability segment $P_1$ (period T/2).

Control of this stepping motor 8, and also control of the permeability meter 6 and of the measuring head 2, are effected by a processor located in the housing of the permeability meter 6. This processor can be connected with advantage to several peripherals such as a display unit 10, a printer 11, or a floppy disc or CD ROM drive 12.

Of course this processor can also be programmed so as to effect a sinusoidal regression in order to determine the ends of a sinusoid (values for which the derivative cancels out and signed by the second derivative for these values).

Figure 4:
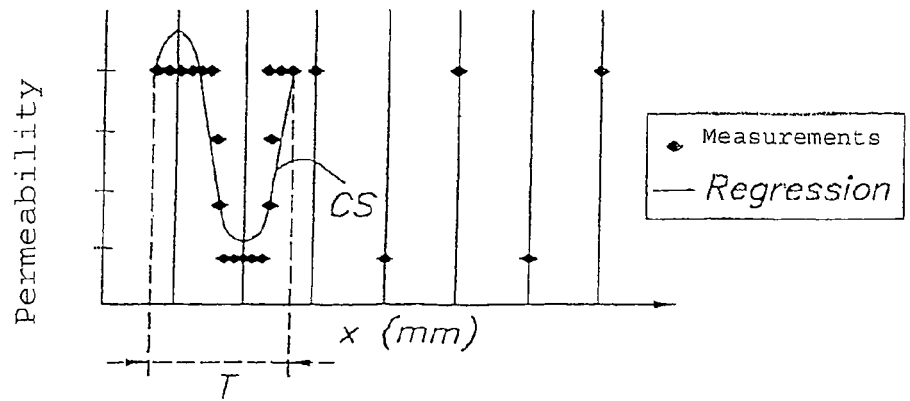
FIG. 4 is a diagram indicating the permeability measurement points obtained during the stage for determination of the permeability profile, and the corresponding regression curve.

According to the method of the invention, before performing the permeability measurement on successive segments of the strip, the device must execute a preliminary positioning steps, consisting of the following steps:

A stage consisting of measuring the permeability millimeter-by-millimeter over a length of the strip equal to the sum of a segment width of low permeability and a segment width of high permeability (period T). The measurement points are shown by diamonds on the diagram of FIG. 4.

To this end, the stepping motor 8 is switched to its first mode of operation (advanced millimeter-by-millimeter). During this stage, the measured permeability values, together with the information relating to the position of the strip 1, are stored in the processor's memory.

A second stage in which the processor determines a sunusoidal curve CS which consists with the values read off during the first stage.

A third stage in which the processor determines the abscissa of the two ends of the sinusoidal curve CS thus obtained, which correspond to the transverse median axes AT of two successive segments $P_1$ and $P_2$ of the strip 1.

A fourth stage, in which the processor determines the difference between the abscissa of the second end and the axis OO' of the measuring head 2, and orders a movement of the strip 1 so as to cause the said abscissa and the said axis OO' to coincide, thereby achieving the desired positioning.

Once the preliminary stage has been completed, the device begins the measurement phase. To this end, the stepping motor 8 is switched into its second mode of operation (period T/2).

At each step, the measuring head 2 is located opposite to the transverse median axis AT of a segment $P_1$ or $P_2$, and the permeability meter measures the permeability. The result of this measurement is then stored in memory, together with the data relating to the position of the strip 1.

This information can then be viewed on the display unit and/or printed on the printer, so that checks can be performed.

As mentioned previously, determination of the sinusoid CS is achieved by means of a regression calculation which is employed to obtain a sinusoidal curve using the expression:

$$Y = A_0 + (A_1)\cos(2\pi x/T) + (B_1)\sin(2\pi x/T)$$

in which $A_0$, $A_1$ and $B_1$ are the coefficients to be determined, x is the abscissa (which expresses a length varying from 0 to T)

y is the ordinate (which expresses the permeability).

Coefficients $A_0$, $A_1$ and $B_1$ are then obtained through the following expressions:

$$A_0 = (1/T)\Sigma Y_1$$

$$A_1 = (1/T)\Sigma(Y_1 \cos(2\pi X_i/T))$$

$$B_1 = (2/T)\Sigma(Y_1 \sin(2\pi X_i/T))$$

in which i is an index which varies from 1 to T, xi and yi are the values of x and y for a particular value of i.

From these expressions, it is possible to deduce the following relations:

if $A_i = 0$ then $X = T/4$, else $X = (T/2\pi)\arctan(B_i/A_i)$ if $X < 0$ $X = X + T/2$ if $B_1 < 0$ X is a maximum (high permeability)

if $B_1 = 0$ X is a minimum (low permeability)

Of course, the invention is not limited to this method of calculation, given that many solutions are capable of reaching similar results.

The invention claimed is:

1. Method for automatic determination of the permeability of a sheet or a strip of porous material consisting of successive segments which present different levels of permeability, alternately and with a pre-establishing periodicity T, where this method implements a permeability meter consisting of a measuring head in relation to which the said sheet or strip can be moved in steps, said method comprising:

a preliminary positioning stage, with determination of a permeability profile of the sheet or strip over a length of material corresponding to at least the period T, which comprises two successive segments, determination of a sinusoid from the profile obtained, determination of the position of the two ends of this sinusoid, and centring of the measuring head at the second end, and a measurement stage following centring of the head, consisting of the advance, step by step, of the sheet or strip in steps of T/2, with a permeability measurement at each step.

2. Method according to claim 1, wherein determination of the permeability profile is achieved by performing a succession of permeability measurements in a period which is very much less than period T.

3. Method according to the claim 1, wherein said strip consists of a cigarette paper with two alternating series of segments with two different permeabilities, these segments located perpendicularly to the longitudinal axis of the strip.

4. Method according to the claim 1, wherein determination of the said sinusoid is effected by means of a regression based on the values obtained during determination of the permeability profile.

5. Method according to claim 4, wherein said regression is obtained using the method of least squares.

6. Device for automatic determination of the permeability of a sheet or a strip of porous material consisting of successive segments which present different levels of permeability, alternately and with a pre-established periodicity T, said device having a permeability meter consisting of a measuring head in relation to which the said sheet or strip can be moved in steps, said measuring head having two tubular parts between which the said strip passes, these two parts being movable in relation to each other so that they can grasp the strip between their edges, a stepping motor for moving said strip said stepping motor being designed to operate in either of two modes, namely a first mode moving millimeter by millimeters, and a second mode where the step corresponds to half of the sum of the widths of two consecutive segments and a processor for controlling the stepping motor and for controlling the movements of the measuring head.

7. Device according to claim 6, wherein said processor is programmed so that it can calculate the aforementioned sinusoid as well as the ends of this sinusoid.

* * * * *